Figure 1:
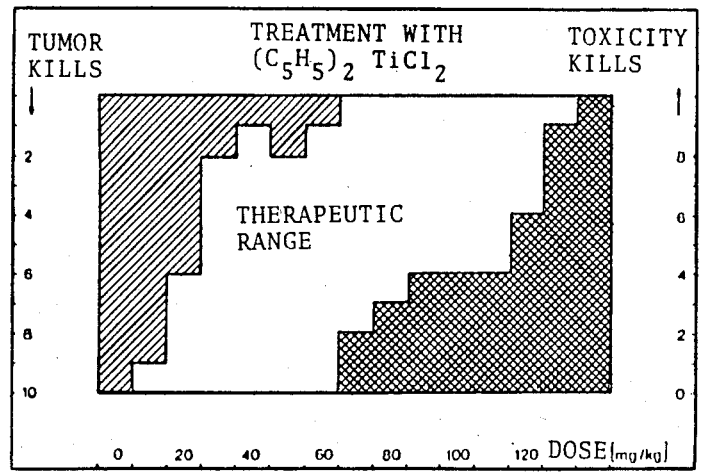

United States Patent [19]

Köpf et al.

[11] Patent Number: 4,608,387

[45] Date of Patent: Aug. 26, 1986

[54] USE OF CYCLOPENTADIENYL METAL-ACIDO COMPLEXES FOR THE TREATMENT OF CANCER AND PHARMACEUTICAL COMPOSITIONS CONTAINING SAID COMPLEXES

[76] Inventors: Hartmut Köpf; Petra Köpf-Maier, both of Bundesring 33, D-1000 Berlin 42, Fed. Rep. of Germany

[21] Appl. No.: 538,539

[22] Filed: Oct. 3, 1983

Related U.S. Application Data

[63] Continuation of Ser. No. 135,442, Mar. 31, 1980, abandoned.

[30] Foreign Application Priority Data

Jun. 8, 1979 [DE] Fed. Rep. of Germany ....... 2923334

[51] Int. Cl.⁴ .............................................. A61K 31/28
[52] U.S. Cl. .................................................. 514/492
[58] Field of Search ......................... 424/287; 514/492

[56] References Cited

U.S. PATENT DOCUMENTS

| | | | |
|---|---|---|---|
| 2,882,288 | 4/1959 | Brantley et al. | 260/429 C X |
| 2,983,741 | 5/1961 | Brantley | 260/429 C X |
| 3,080,305 | 3/1963 | Gorsich | 260/429 C X |
| 3,152,157 | 10/1964 | Shapiro et al. | 260/429 C X |
| 3,161,629 | 12/1964 | Gorsich | 260/429 C X |

OTHER PUBLICATIONS

Feld et al., The Organic Chemistry of Titanium, Washington–Butterworths, 1965, pp. 12–14.
Wailes et al., Organometallic Chemistry of Titanium, Zirconium, Hafnium, Academic Press, N.Y., N.Y., 1974, pp. 52 and 53.

*Primary Examiner*—Jerome D. Goldberg
*Attorney, Agent, or Firm*—Birch, Stewart, Kolasch & Birch

[57] ABSTRACT

This disclosure relates to the use of cytostatically active cyclopentadienyl metal-acido complexes for the treatment of transplanted tumor and pharmaceutical compositions containing said complexes. The organometallic compounds employed in the invention have the general formula:

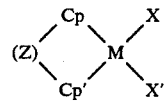

wherein M is Ti, Zr, Hf, V, Nb, Ta, Mo or W, Cp and Cp' are, e.g., cyclopentadienyl or substituted cyclopentadienyl radicals, Z is an optional straight-chain or branched bridging group having 1 to 3 C, Si or Ge atoms in the bridging chain and X and X' are, e.g., halogen, cyanate, isocyanate, thiocyanate, isothiocyanate, azide or phenylacetylide.

16 Claims, 3 Drawing Figures

▨ Tumor kills without indication of compound toxicity

▩ Toxicity kills (kills within 8 days after transplant of the tumor without macroscopically detectable tumor growth)

☐ Surviving animals (therapeutic range)

USE OF CYCLOPENTADIENYL METAL-ACIDO COMPLEXES FOR THE TREATMENT OF CANCER AND PHARMACEUTICAL COMPOSITIONS CONTAINING SAID COMPLEXES

This application is a continuation of copending application Ser. No. 135,442, filed on Mar. 31, 1980, now abandoned.

BACKGROUND OF THE INVENTION

1. Field of the Invention

The present invention relates to the use of cytostatically active cyclopentadienyl metal-acido complexes for the treatment of transplanted tumor and pharmaceutical compositions containing said complexes.

2. Description of the Prior Art

Metal-containing compounds having cytostatic efficacy have been known heretofore only in primarily inorganic complexes of the type of platinum(II) cis-dichlorodiammines of the following formula:

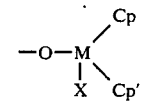

These complexes do not contain any organic groups bound directly to a metal atom via a carbon atom and therefore are not organometallic compounds.

SUMMARY OF THE INVENTION

It has now been found for the first time in accordance with the present invention that a certain group of organometallic compounds exhibits cytostatic activity in animal experiments. These compounds are cyclopentadienyl metal-acido complexes having the following general formula:

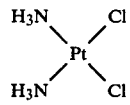

wherein
M is Ti, Zr, Hf, V, Nb, Ta, Mo, or W;
Cp and Cp', being identical or different, are cyclopentadienyl radicals $C_5H_5$ or substituted cyclopentadienyl radicals $C_5H_{5-n}R_n$, wherein the substitutents R have the same or different meanings and represent alkyl (n = 1, 2, 3, 4, or 5), cycloalkyl (n = 1 or 2), aralkyl (n = 1 or 2), trialkylsilyl, tricycloalkylsilyl, or triaralkylsilyl (n = 1 or 2), or germyl, i.e., —GeR$_3'$ wherein R' is alkyl, cycloalkyl or aralkyl, more specifically, trialkylgermyl, tricycloalkylgermyl, or triaralkylgermyl (n = 1 or 2), or wherein the two substituents R together form an indenyl or tetrahydroindenyl structure; or wherein either Cp or Cp' has one of the meanings indicated for X;
(Z) is an optional group bridging Cp and Cp' selected from the group of straight-chain or branched alkylene or equivalent groups having 1 to 3 carbon atoms, preferably 1 carbon atom, in the bridging chain, the carbon atoms in said bridging chain being optionally replaced totally or partly by Si or Ge, and the remaining valences of said C, Si and Ge atoms being saturated by H or alkyl groups;
X and X', being identical or different, are negatively univalent halogenide or pseudohalogenide ligands, or X' is the grouping

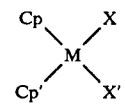

wherein M, X, Cp and Cp' have the above-indicated meanings.

When the optional Z bridging group is not present, the cyclopentadienyl metal-acido complexes can be represented by the following general formula:

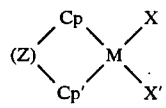

wherein M, Cp, Cp', X and X' are as defined above.

In the mono- or polysubstituted cyclopentadienyl radicals $C_5H_{5-n}R_n$, n represents an integer from 1 to 5. The term "alkyl" is understood to mean straight-chain or branched alkyl residues of 1-10, preferably 1-6, and especially 1-4 carbon atoms. Specific examples are methyl, ethyl, isopropyl, n-butyl, tert.-butyl, 2-ethylhexyl and n-decyl.

The term "cycloalkyl" means cycloaliphatic residues of 3-8, preferably 3-6, and especially 6 carbon atoms. Specific examples are cyclopropyl, cyclobutyl, cyclohexyl, cycloheptyl, and cyclooctyl.

The term "aralkyl" means residues derived from the aforementioned alkyl residues, the aryl groups thereof containing 6-18, preferably 6-14, and especially 6-10 carbon atoms. Preferably, the aralkyl residues carry a prochiral grouping in the 1-position. Specific examples are benzyl, α-phenylethyl, and β-phenylethyl.

The silyl germyl substituents are derived from the above-mentioned alkyl, cycloalkyl, and aralkyl residues.

Specific examples for halogenide ligands X and X' are halogens such as fluoride, chloride, bromide, and iodide.

Specific examples for pseudohalogenide ligands X and X' are cyanate, isocyanate, thiocyanate, isothiocyanate, azide, and phenylacetylide.

Representative examples of the cyclopentadienyl metal-acido complexes according to this invention are as follows:

$(C_5H_5)_2TiF_2$
$(C_5H_5)_2TiFCl$
$(C_5H_5)_2TiCl_2$
$(C_5H_5)_2TiBr_2$
$(C_5H_5)_2TiI_2$
$(C_5H_5)_2Ti(OCN)_2$
$(C_5H_5)_2Ti(NCS)_2$
$(C_5H_5)_2Ti(C_2C_6H_5)_2$
$(C_5H_2)(C_5H_4CH_3)TiF_2$
$(C_5H_5)(C_5H_4CH_3)TiCl_2$
$(C_5H_5)(C_5H_4C_2H_5)TiCl_2$
$(C_5H_5)[C_5H_3(CH_2)_4]TiCl_2$
$(C_5H_5)(C_9H_7)TiCl_2$
$(C_5H_5)[C_5H_4Si(CH_3)_3]TiCl_2$ ($C_5H_4CH_3$)$_2$TiCl$_2$
($C_5H_4$—tert.—$C_4H_9$)$_2$TiCl$_2$
($C_5H_4$—tert.—$C_4H_9$)$_2$Ti(NCS)$_2$
[$C_5H_4CH(CH_3)C_6H_5$]$_2$TiCl$_2$
[$C_5H_3(CH_2)_4$]$_2$TiCl$_2$
($C_9H_7$)$_2$TiCl$_2$
[$C_5H_4Si(CH_3)_3$]$_2$TiF$_2$
[$C_5H_4Si(CH_3)_3$]$_2$TiCl$_2$
[$C_5H_4Si(CH_3)_3$]$_2$TiBr$_2$
[$C_5H_4Si(CH_3)_3$]$_2$TiI$_2$
[$C_5H_4Si(CH_3)_3$]$_2$Ti(NCS)$_2$
[$C_5H_4Si(CH_3)_2$—n—$C_4H_9$]$_2$TiCl$_2$
[$C_5H_4Ge(CH_3)_3$]$_2$TiCl$_2$
$C_5H_5$TiCl$_3$
$C_5H_5$Ti(NCS)$_3$
$C_5(CH_3)_5$TiCl$_3$
($C_5H_5$)$_4$Ti$_2$Br$_2$O
[$C_5H_4Si(CH_3)_3$]$_2$ZrCl$_2$
($C_5H_4$)$_4$Zr$_2$I$_2$O
[$C_5H_4Ge(CH_3)_3$]$_2$HfCl$_2$
($C_5H_5$)$_2$VCl$_2$
($C_5H_2$)$_2$VBr$_2$
($C_5H_5$)$_2$V(NCO)$_2$
($C_5H_5$)$_2$V(NCS)$_2$
($C_5H_4CH_2$—α—$C_{10}H_7$)$_2$V(N$_3$)$_2$
[$C_5H_4Si(CH_3)_2$—n—$C_4H_9$]$_2$VCl$_2$
($C_5H_5$)$_2$NbCl2
($C_5H_5$)$_2$TaCl$_2$
($C_5H_5$)$_2$MoCl$_2$
($C_5H_5$)$_2$MoBr$_2$
($C_5H_5$)$_2$Mo(NCS)$_2$
($C_5H_4C_6H_{11}$)$_2$Mo(N$_3$)Cl
($C_5H_5$)$_2$W(NCO)$_2$
($C_5H_5$)$_2$W(SCN)NCS In the above formulae, $C_9H_7$ is indenyl and $C_5H_3(CH_2)_4$ is tetrahydroindenyl.

The cyclopentadienyl metal-acido complexes employed in the present invention are known or can be prepared according to conventional methods; see, for example, Wilkinson et al., *J. Amer. Chem. Soc.*, 76: 4281 (1954); or Sullivan et al, *J. Organometal. Chem.* 8: 277 (1967). The bridged complexes can be prepared by the processes described in the following references. Köpf et al, *J. Organometal. Chem.*, 64: C 37 (1974); and Hillman et al, *J. Organometal, Chem.*, 42: 123 (1972).

In accordance with the present invention, it has been determined that the cyclopentadienyl metal-acido complexes described herein exhibit cancerostatic activity in animal tests. The testing procedure was as follows.

Female CF$_1$ mice were each injected intraperitoneally with approximately 6·10$^6$ Ehrlich-ascites tumor cells and, 24 hours later, received a one-time introperitoneal administration of the organometallic compound (dosage range 10–500 mg./kg.). In each case, 5–10 animals were tested per dose. To provide for an exact dosage of the compounds, which were frequently administered in a suspension, a solubilizer such as dimethyl sulfoxide was added to the injection fluid. A mode of administration which proved to be advantageous comprised dissolving or suspending the individual amounts of the compound in 0.4 ml. of a liquid mixture of dimethyl sulfoxide and physiological NaCl (saline) solution in a volume ratio of 1:9 with 5 minutes of ultrasonic treatment, and then injecting the resulting solution or suspension.

In case of complexes showing an acidic reaction by hydrolysis, especially titanium complexes, local irritation at the site of injection was avoided by simultaneously buffering to pH 4–7, for example, with sodium bicarbonate or tris(hydroxymethyl)aminomethane.

Each test series included a group of untreated control animals injected intraperitoneally with 0.4 ml. of dimethyl sulfoxide/physiological saline solution (volume ratio 1:9) without administration of the compound (negative control), as well as a group of animals injected introperitoneally with 10 mg./kg. of platinum(II) cis-dichlorodiammine in 0.4 ml. of physiological saline solution after ultrasonic treatment (positive control).

The evaluation of tumor growth in the individual dosage ranges was made by weight curve and survival time. In the case of each test compound, a determination was made of the dosage-dependent number of tumor kills, toxic dose kills, and surviving, cured animals, as well as of the associated percentage increase in the average survival time.

Figure 2:
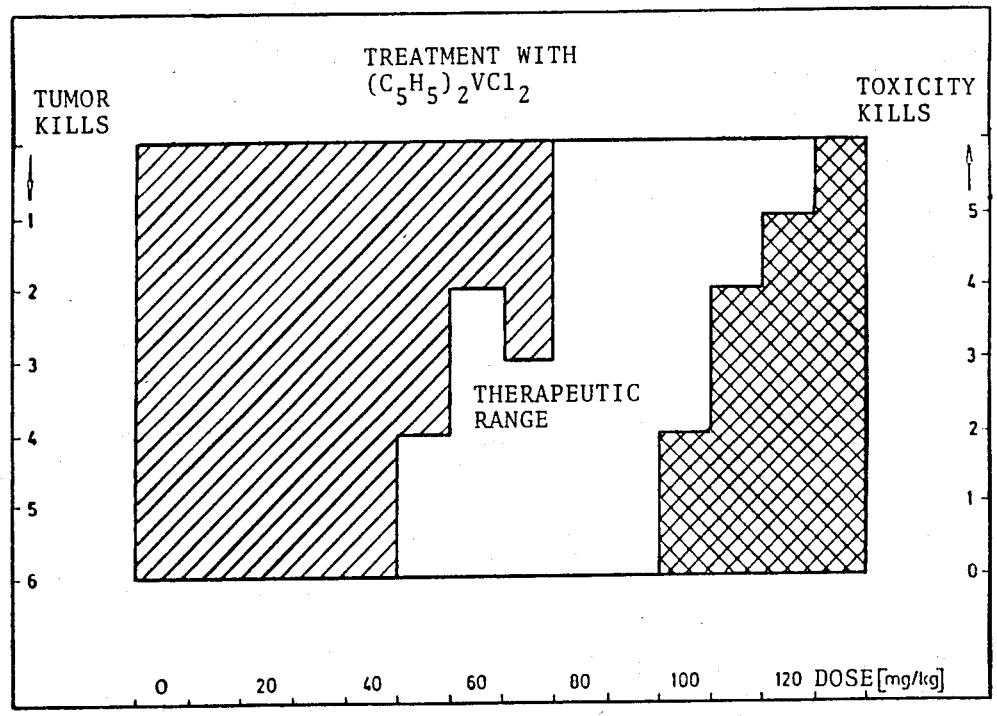
Figure 3:
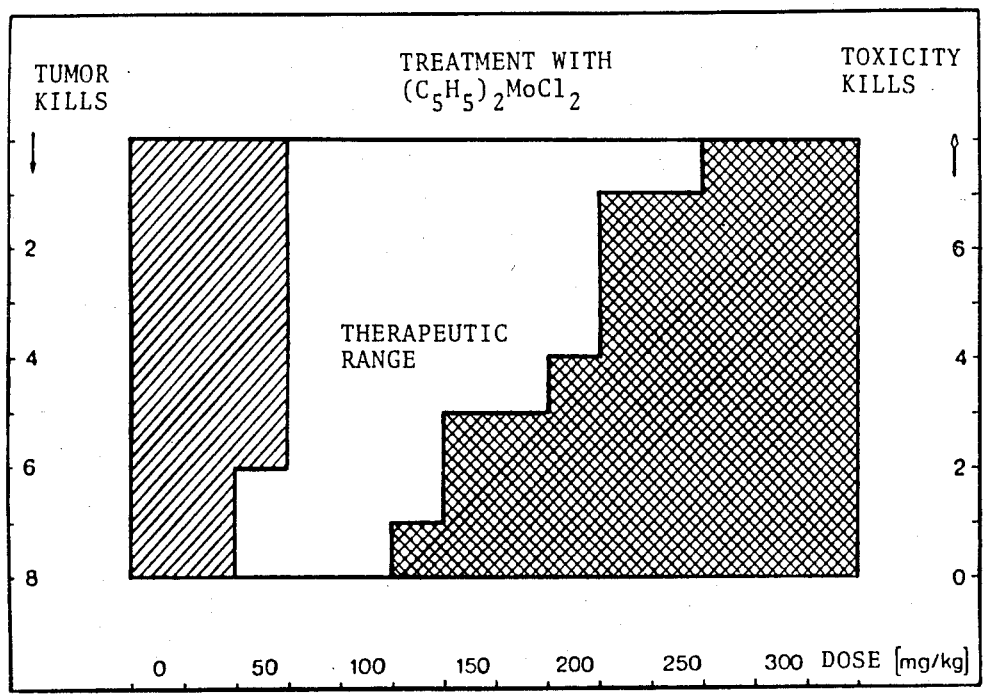

The results obtained in the testing of dichlorobis(η$^5$-cyclopentadienyl) titanium(IV) (titanocene dichloride), dichlorobis (θ$^5$-cyclopentadienyl) vanadium(IV) (vanadocene dichloride), and dichlorobis(θ$^5$-cyclopentadienyl) molybdenum(IV) (molybdocene dichloride) are set forth in Tables I through III and are graphically illustrated in FIGS. 1 through 3.

Table IV shows a compilation of the pharmacological data of the aforementioned cyclopentadienyl metal-acido complexes, as well as several other complexes of this invention.

Table V shows the results obtained with cyclopentadienyl titanium-acido complexes after buffering the injection solutions with 0.1 molar NaHCO$_3$ to a pH of between 5.0 and 5.5.

TABLE I

Effect of ($C_5H_5$)$_2$TiCl$_2$ on the Survival Time of Mice Carrying Ehrlich-Ascites Tumor

| Dose (mg/kg) | Number of Test Animals | Number of Tumor Kills | Number of Toxicity Kills | Surviving Animals Number | Proportion (a) (%) | Average Survival Time (a) (days) | Increase in Average Survival Time (a) (b) (%) |
|---|---|---|---|---|---|---|---|
| 10 | 10 | 9 | 0 | 1 | 10 | 21.6 | +39.4 |
| 20 | 10 | 6 | 0 | 4 | 40 | 45.6 | +194.2 |
| 30 | 10 | 2 | 0 | 8 | 80 | 74.4 | +380.0 |
| 40 | 10 | 1 | 0 | 9 | 90 | 82.2 | +430.3 |
| 50 | 10 | 2 | 0 | 8 | 80 | 74.5 | +380.6 |
| 60 | 10 | 1 | 0 | 9 | 90 | 82.9 | +434.8 |
| 70 | 10 | 0 | 2 | 8 | 80 | 72.5 | +367.7 |
| 80 | 10 | 0 | 3 | 7 | 70 | 63.8 | +311.6 |
| 90 | 10 | 0 | 4 | 6 | 60 | 56.3 | +263.2 |
| 100 | 10 | 0 | 4 | 6 | 60 | 55.5 | +258.1 |

TABLE I-continued

Effect of $(C_5H_5)_2TiCl_2$ on the Survival Time of Mice Carrying Ehrlich-Ascites Tumor

| Dose (mg/kg) | Number of Test Animals | Number of Tumor Kills | Number of Toxicity Kills | Surviving Animals Number | Proportion (a) (%) | Average Survival Time (a) (days) | Increase in Average Survival Time (a) (b) (%) |
| --- | --- | --- | --- | --- | --- | --- | --- |
| 110 | 10 | 0 | 4 | 6 | 60 | 55.8 | +260.0 |
| 120 | 10 | 0 | 6 | 4 | 40 | 38.3 | +147.1 |
| 130 | 10 | 0 | 9 | 1 | 10 | 12.7 | −18.1 |
| 140 | 10 | 0 | 10 | 0 | 0 | 3.2 | −79.4 |

(a) Up to the target date (90th day after transplant).
(b) Based on the untreated control animals (average survival time 15.5 days).

TABLE II

Effect of $(C_5H_5)_2VCl_2$ on the Survival Time of Ehrlich-Ascites Tumor-Carrying Mice

| Dose (mg/kg) | Number of Test Animals | Surviving Animals Number | Proportion (a) (%) | Average Survival Time (a) (days) | Increase in Average Survival Time (a) (b) % |
| --- | --- | --- | --- | --- | --- |
| 10 | 6 | 0 | 0 | 15.7 | −5.4 |
| 20 | 6 | 0 | 0 | 13.3 | −19.9 |
| 30 | 6 | 0 | 0 | 14.7 | −11.4 |
| 40 | 6 | 0 | 0 | 16.0 | −3.6 |
| 50 | 6 | 2 | 33 | 20.3 | +22.3 |
| 60 | 6 | 4 | 67 | 24.0 | +44.6 |
| 70 | 6 | 3 | 50 | 22.8 | +37.3 |
| 80 | 6 | 6 | 100 | 30.0 | +80.7 |
| 90 | 6 | 6 | 100 | 30.0 | +80.7 |
| 100 | 6 | 4 | 67 | 20.7 | +24.7 |
| 110 | 6 | 2 | 33 | 11.7 | −29.5 |
| 120 | 6 | 1 | 17 | 7.2 | −56.6 |
| 130 | 6 | 0 | 0 | 2.3 | −86.1 |

(a) Up to the target date (30th day after transplant).
(b) Based on the untreated control animals (average survival time 16.6 days).

TABLE III

Effect of $(C_5H_5)_2MoCl_2MoCl_2$ on the Survival Time of Ehrlich-Ascites Tumor-Carrying Mice

| Dose (mg/kg) | Number of Test Animals | Surviving Test Animals Number | Proportion (a) (%) | Average Survival Time (a) (days) | Increase in Average Survival Time (a) (b) (%) |
| --- | --- | --- | --- | --- | --- |
| 25 | 8 | 0 | 0 | 13.5 | −14.0 |
| 50 | 8 | 2 | 25 | 17.0 | +8.3 |
| 75 | 8 | 8 | 100 | 30.0 | +91.1 |
| 100 | 8 | 8 | 100 | 30.0 | +91.1 |
| 125 | 8 | 7 | 88 | 26.6 | +69.4 |
| 150 | 8 | 5 | 63 | 19.5 | +24.2 |
| 175 | 8 | 5 | 63 | 19.7 | +25.5 |
| 200 | 8 | 4 | 50 | 16.1 | +2.5 |
| 225 | 8 | 1 | 13 | 5.8 | −63.1 |
| 250 | 8 | 1 | 13 | 6.0 | −61.8 |
| 275 | 8 | 0 | 0 | 1.7 | −89.2 |
| 300 | 8 | 0 | 0 | 1.5 | −90.4 |
| 325 | 8 | 0 | 0 | 1.3 | −91.7 |

(a) Up to the target date (30th day after transplant).
(b) Based on the untreated control animals (average survival time 15.7 days).

TABLE IV

Pharmacological Data for Several Cyclopentadienyl Metal-Acido Complexes Tested on Mice Carrying Ehrlich-Ascites Tumor

| Compound | Experimental Dosage Range (mg/kg) | Dosage Range with Optimum Therapeutic Effect (mg/kg) | Curative Rate in the Optimum Dosage Range (%) | Lethal Dose in 50% ($LD_{50}$) (mg/kg) | Lethal Dose in 100% ($LD_{100}$) (mg/kg) |
| --- | --- | --- | --- | --- | --- |
| $(C_5H_5)_2TiF_2$ | 10–120 | 40 | 90 | 70 | 100 |
| $(C_5H_5)_2TiFCl$ | 10–120 | 50–60 | 90 | 80 | 100 |
| $(C_5H_5)_2TiCl_2$ | 10–140 | 40–70 | 80–90 | 110 | 140 |
| $(C_5H_5)_2TiBr_2$ | 10–180 | 60–100 | 100 | 140 | 180 |
| $(C_5H_5)_2TiJ_2$ | 10–180 | 60–100 | 100 | 140 | 180 |
| $(C_5H_5)_2Ti(NCS)_2$ | 10–240 | 60–80 | 100 | 120 | 200 |
| $(C_5H_5)_2VCl_2$ | 10–130 | 80–90 | 100 | 110 | 130 |

TABLE IV-continued
Pharmacological Data for Several Cyclopentadienyl Metal-Acido Complexes Tested on Mice Carrying Ehrlich-Ascites Tumor

| Compound | Experimental Dosage Range (mg/kg) | Dosage Range with Optimum Therapeutic Effect (mg/kg) | Curative Rate in the Optimum Dosage Range (%) | Lethal Dose in 50% ($LD_{50}$) (mg/kg) | Lethal Dose in 100% ($LD_{100}$) (mg/kg) |
|---|---|---|---|---|---|
| $(C_5H_5)_2MoCl_2$ | 25–325 | 75–100 | 100 | 200 | 275 |
| $(C_5H_5)_2NbCl_2$ | 5–50 | 20–25 | 100 | 35 | 45 |
| $(C_5H_5)_2TaBr_2$ | 10–260 | 90–140 | 25–50 | 200 | 260 |
| $(C_5H_5)_2WCl_2$ | 25–750 | 100–525 | 10–20 | 500 | 650 |
| Mono-cyclopentadienyl-Complexes | | | | | |
| $(C_5H_5)TiCl_3$ | 10–180 | 50–60 | 10–20 | 100 | 150 |
| $(C_5H_5)Ti(NCS)_3$ | 10–150 | 70–100 | 20–30 | 130 | 150 |
| Monosubstituted Complexes | | | | | |
| $(C_5H_5)[(C_5H_4Si(CH_3)_3]TiCl_2$ | 10–120 | 40–80 | 70–80 | 100 | 120 |
| $(C_5H_5)(C_5H_4C_2H_5)TiCl_2$ | 10–120 | 50–80 | 50–60 | 100 | 120 |
| 1,1'-Disubstituted Complexes | | | | | |
| $[C_5H_4Si(CH_3)_3]_2TiCl_2$ | 10–460 | 260–300 | 10 | 360 | 420 |
| $[C_5H_4Si(CH_3)_2\text{-}n\text{-}C_4H_9]_2TiCl_2$ | 10–460 | 320–360 | 10–20 | 420 | 460 |
| $[C_5H_4Ge(CH_3)_3]_2TiCl_2$ | 10–460 | 240–320 | 20–30 | 400 | 450 |
| Bridged 1,1'-disubstituted Complexes | | | | | |
| $(CH_3)HC(C_5H_4)_2TiCl_2$ | 10–400 | 180–200 | 10–20 | 300 | 360 |
| $(CH_3)HSi(C_5H_4)_2TiCl_2$ | 10–400 | 140–180 | 30 | 280 | 360 |
| $(C_2H_5)_2Si(C_5H_4)_2TiCl_2$ | 10–400 | 160–180 | 20 | 260 | 340 |
| $(CH_3)_2Ge(C_5H_4)_2TiCl_2$ | 10–400 | 180–200 | 10–20 | 320 | 400 |
| Indenyl Complexes | | | | | |
| $(C_9H_7)_2TiCl_2$ | 10–400 | 180–200 | 10–20 | 360 | 400 |
| $[C_5H_3(CH_2)_4]_2TiCl_2$ | 10–400 | 260–280 | 10–20 | 330 | 360 |
| $[C_5H_3(CH_2)_4](C_5H_5)TiCl_2$ | 10–220 | 90–100 | 30–60 | 120 | 140 |
| O-Bridged Complex | | | | | |
| $[(C_5H_5)_2TiCl]_2O$ | 10–250 | 90–140 | 30 | 190 | 240 |

TABLE V
Pharmacological Data for Cyclopentadienyl Titanium-Acido Complexes after Buffering the Injected Solutions with 0.1 molar $NaHCO_3$ to pH 5.0–5.5

| Compound | Experimental Dosage Range (mg/kg) | Dosage Range with Optimum Therapeutic Effect (mg/kg) | Curative Rate in the Optimum Dosage Range (%) | Lethal Dose in 50% ($LD_{50}$) (mg/kg) | Lethal Dose in 100% ($LD_{100}$) (mg/kg) |
|---|---|---|---|---|---|
| $(C_5H_5)_2TiF_2$ | 10–120 | 30–40 | 100 | 65 | 90 |
| $(C_5H_5)_2TiCl_2$ | 10–180 | 60–100 | 100 | 130 | 180 |
| $(C_5H_5)_2TiBr_2$ | 10–360 | 100–120 | 100 | 200 | 320 |
| $(C_5H_5)_2TiI_2$ | 10–240 | 80–130 | 100 | 185 | 240 |
| $(C_5H_5)_2Ti(NCS)_2$ | 10–240 | 140 | 100 | 200 | 220 |
| $(C_5H_5)TiCl_3$ | 10–250 | 110–140 | 20–30 | 200 | 240 |

As demonstrated by the above results, the cyclopentadienyl metal-acido complexes of the invention are highly efficacious anti-tumor agents against transplanted tumors with a curative rate in the therapeutic range of 80–100%. The cancerostatic activity of these complexes corresponds at least to that of platinum(II) cis-dichlorodiammine, which likewise inhibits tumor development in all mice in the above-described tests in the optimum dosage as a positive control.

Therefore, the primary objectives of the present invention relate to medicinal agents having a cancerostatic effect characterized in that they contain at least one cyclopentadienyl metal-acido complex of general Formula (I) as the active anticancer agent in addition to pharmaceutically compatible vehicles, diluents and/or excipients, and to the use of such agents in combatting cancer.

The pharmaceutical preparation of the active anticancer agents is preferably effected in unit dosage forms adapted to the respective type of administration. A unit dosage can be, for example, a tablet, a capsule, a suppository, or a measured volume quantity of a powder, granules, or a solution or suspension. The term "unit-dosage" is understood to mean a physically determined unit containing an individual amount of the active agent in mixture with a suitable pharmaceutical vehicle, carrier, diluent and/or excipient. In this connection, the amount of active agent is selected so that one or several units are usually sufficient for a single therapeutic administration. The unit dosage can also be in subdivided form, e.g., in the form of notched tablets, if only a fraction, for example one-half or one-quarter, of the subdivided unit is required for an individual therapeutic administration. If present in unit dosage form, the medicinal agents of the invention contain 1 mg. to 10,000 mg., preferably 5 mg. to 7,500 mg., of active agent.

The medicinal agents of the invention are preferably applied orally, rectally, or parenterally, e.g., intravenously (i.v.), subcutaneously, intramuscularly, intrapleurally, intraperitoneally, intrafocally, or perifocally. The therapeutic administration can take place by means of infusion continuously over a period of several hours, or by single or repeated individual dosages or individual injections. The sequence of administrations and the dosage administered can vary greatly in dependence on the nature and stage of the disease, as well as in dependence on the treatment regime, especially the number and dosage level of combination preparations administered. For example, it is possible to initiate the treatment with daily doses of 200–800 mg. i.v. or with individual doses, e.g. 10–40 mg./kg. i.v., in corresponding intervals, followed by a long-term daily treatment with 1–4 tablets with 50 mg. of active agent each.

The pharmaceutical compositions normally consist of the active agents of this invention and nontoxic, pharmaceutically acceptable vehicles used as an admixture in solid, semisolid, or liquid form, or as an encasing composition, for example, in the form of a capsule, a tablet coating, a bag, or some other container for the active agent. In this connection, the vehicle can serve, for example, as an intermediary for the medicine absorption by the body, as an auxiliary formulating agent, sweetener, flavor-ameliorating agent, coloring agent, or preservative.

Suitable for oral administration are, for example, tablets, dragees, hard and soft gelatin capsules, dispersible powders, granules, aqueous and oil suspensions, emulsions, solutions, and syrups.

Tablets can contain inert diluents, such as calcium carbonate, calcium phosphate, sodium phosphate, or lactose; granulating and distributing agents, such as corn starch or alginates; binders, such as amylose, gelatin, or acacia gum; and lubricants, such as aluminum stearate or magnesium stearate, talc, or silicone oil. Optionally, the tablets are provided with a coating which can also have such a character that it effects a delayed dissolution and resorption of the medicinal agent in the gastrointestinal tract and thus, for example, provides improved compatibility or a longer duration of effectiveness.

Gelatin capsules can contain the active agent in a mixture with a solid diluent (e.g., calcium carbonate or kaolin) or an oily diluent (e.g., olive, peanut, or paraffin oil).

Suitable suspension agents are, for instance, sodium carboxymethylcellulose, methylcellulose, hydroxypropylcellulose, sodium alginate, polyvinylpyrrolidone, tragacanth gum, or acacia gum; suitable dispersing and wetting agents are, for example, polyoxyethylene stearate, heptadecaethyleneoxycetanol, polyoxyethylene sorbitol monooleate, polyoxyethylene sorbitan monooleate, or lecithin; suitable preservatives are, for example, methyl or propyl hydroxybenzoate; suitable flavoring agents or sweeteners are, for instance, sucrose, lactose, dextrose, or invert sugar syrup.

Oily suspensions can contain, for example, peanut, olive, sesame, coconut, or paraffin oil, as well as thickeners, such as beeswax, hard paraffin, or cetyl alcohol, sweeteners, flavoring agents and/or antioxidants.

Water-dispersible powders and granules contain the active agent in a mixture with dispersing, wetting, and suspension agents, e.g., the aforementioned materials and/or dimethyl sulfoxide, as well as in a mixture with sweeteners, flavoring agents and/or coloring agents.

Emulsions can contain, for example, olive, peanut, or paraffin oil in addition to emulsifiers, such as acacia gum, tragacanth gum, phosphatides, sorbitan monooleate, or polyoxyethylene sorbitan monooleate, sweeteners and/or flavoring agents.

Suitable for rectal application are suppositories produced with the aid of binders melting at rectal temperature, for example, cocoa butter or polyethylene glycols.

The medicinal agents can be used parenterally as sterile isotonic sodium chloride solutions or other solutions. To attain uniform dissolution or suspension, a solubilizer is preferably added, such as dimethyl sulfoxide.

In all forms of administration, the medicinal agents of this invention can furthermore contain buffer substances, e.g., sodium bicarbonate or tris(hydroxymethyl)aminomethane.

In addition to the cyclopentadienyl metal-acido complexes employed in this invention, the medicinal agents can contain one or more other pharmacologically active components of other cytostatically effective groups of medicines, e.g., alkylating agents or anti-metabolites, as well as cytostatic alkaloids, antibiotics, enzymes, and heavy metal compounds. Furthermore, the medicinal agents can optionally contain substances having an immunopressive effect and vitamins. The above-mentioned additives can also be added in separate pharmaceutical preparations in the form of combination preparations to the active agents of the present invention.

The active agent content in the pharmaceutical compositions of the invention is ordinarily 0.01–95% by weight, preferably 0.1–85% by weight, based on the finished medicine, i.e., the final pharmaceutical formulation.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A pharmaceutical composition, consisting essentially of: 0.01 to 95% by weight of a cyclopentadienyl metal-acido complex selected from the group consisting of $(C_5H_5)_2TiX_2$, $(C_5H_5)_2VX_2$, $(C_5H_5)_2MoX_2$, $(C_5H_5)_2NbX_2$, $(C_5H_5)_2TaX_2$, $(C_5H_5)_2WX_2$, $(C_5H_5)TiX_3$, $(C_5H_5)_2Ti(NCS)_2$, $(C_5H_5)TI(NCS)_3$, $(C_5H_5)(C_5H_4C_2H_5)TiX_2$, $[C_5H_4Ge(CH_3)_3]_2TiX_2$, $(CH_3)HC(C_5H_4)_2TiX_2$, $(CH_3)_2Ge(C_5H_4)_2TiX_2$, $(C_9H_7)_2TiX_2$, $[C_5H_3(CH_2)_4]_2TiX_2$, $[C_5H_3(CH_2)_4](C_5H_5)TiX_2$ and $[(C_5H_5)_2TiX]_2O$ wherein each X, which may be the same or different, is a halogen atom; and a sterile non-toxic pharmaceutically acceptable vehicle therefor.

2. A pharmaceutical composition according to claim 1, wherein said pharmaceutically acceptable vehicle is selected from the group consisting of tablets, dragees, hard and soft gelatin capsules, dispersible powders, and granules.

3. A pharmaceutical composition according to claim 1, wherein said pharmaceutically acceptable vehicle is a physiological saline solution.

4. A pharmaceutical composition according to claim 1, wherein said pharmaceutically acceptable vehicle is an isotonic sodium chloride solution.

5. A pharmaceutical composition according to claim 1, wherein said carrier is an injectable vehicle.

6. A pharmaceutical composition according to claim 5, wherein said injectable vehicle includes a physiological saline solution as the vehicle and dimethyl sulfoxide as a solubilizer.

7. A pharmaceutical composition according to claim 5, and further including a buffer.

8. A pharmaceutical composition according to claim 7, wherein said buffer is sodium bicarbonate or tris(hydroxymethyl) aminomethane.

9. A pharmaceutical composition according to claim 1, wherein said pharmaceutically acceptable vehicle is an aqueous or oily suspension, emulsion, solution or syrup.

10. A liquid pharmaceutical composition according to claim 1, having a pH of 4-7.

11. An injectable pharmaceutical composition according to claim 5, having a pH between 5.0 and 5.5.

12. A pharmaceutical composition according to claim 5, which contains an aqueous vehicle and a solubilizer.

13. A pharmaceutical composition according to claim 1, wherein said composition is in the form of a suspension containing a liquid vehicle and a dispersing or wetting agent.

14. A pharmaceutical composition according to claim 1, wherein said composition is in the form of an emulsion containing a liquid vehicle and an emulsifier.

15. A pharmaceutical composition according to claim 1, wherein said composition is in the form of a water-dispersible powder or granule which contains said cyclopentadienyl metal-acido complex in a mixture with a dispersing, wetting or suspension agent.

16. A method for the treatment of transplanted tumors in lower animals which comprises injecting into said animal an effective tumor growth inhibiting amount of the composition according to claim 1.

* * * * *